12) United States Patent
Iguchi et al.

(10) Patent No.: US 10,407,463 B2
(45) Date of Patent: Sep. 10, 2019

(54) METHOD FOR PRODUCING ALPHA-FORM CRYSTAL OF REDUCED GLUTATHIONE, AND METHOD FOR STORING SAID CRYSTAL

(71) Applicant: KYOWA HAKKO BIO CO., LTD., Tokyo (JP)

(72) Inventors: Maya Iguchi, Tokyo (JP); Kazunari Fukumoto, Tokyo (JP); Hiroshi Nagano, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 1 day.

(21) Appl. No.: 15/579,592

(22) PCT Filed: Jun. 3, 2016

(86) PCT No.: PCT/JP2016/066586
§ 371 (c)(1),
(2) Date: Dec. 4, 2017

(87) PCT Pub. No.: WO2016/195070
PCT Pub. Date: Dec. 8, 2016

(65) Prior Publication Data
US 2018/0170959 A1 Jun. 21, 2018

(30) Foreign Application Priority Data

Jun. 5, 2015 (JP) .................................. 2015-114855

(51) Int. Cl.
| C07K 5/037 | (2006.01) |
| C07K 1/02 | (2006.01) |
| C07K 1/30 | (2006.01) |
| C07K 5/02 | (2006.01) |
| C07K 5/06 | (2006.01) |
| C07K 5/08 | (2006.01) |

(52) U.S. Cl.
CPC ................ *C07K 1/306* (2013.01); *C07K 1/02* (2013.01); *C07K 5/0215* (2013.01); *C07K 5/06* (2013.01); *C07K 5/08* (2013.01)

(58) Field of Classification Search
None
See application file for complete search history.

(56) References Cited

U.S. PATENT DOCUMENTS

| 8,188,308 B2 | 5/2012 | Shimose et al. |
| 2010/0099847 A1 | 4/2010 | Shimose et al. |

FOREIGN PATENT DOCUMENTS

| JP | S46-029130 B1 | 8/1971 |
| JP | S46-043529 B1 | 12/1971 |
| JP | S61-282397 A | 12/1986 |
| JP | H05-339286 A | 12/1993 |
| JP | 2010-059125 A | 3/2010 |
| JP | 5243963 B2 | 7/2013 |

OTHER PUBLICATIONS

Kuroda et al., "Studies on Drug Nonequivalence. VIII. Solubilities of Polymorphs and Hydrate of Mercaptopurine," *Yakugaku Zasshi*, 99(7): 745-751 (1979).
Momonaga et al., "Additive Effect and Scale-up in Selective Crystallization of Sodium Cefazolin Polymorphs," *Kagaku Kogaku Ronbunshu*, 18(5): 553-561 (1992).
Yamasaki et al., "Analytical studies of polymorphism of glutathione," *Bunseki Kagaku*, 18(7): 874-878 (1969).
Japanese Patent Office, International Search Report in International Patent Application No. PCT/JP2016/066586 (dated Aug. 16, 2016).
Japanese Patent Office, Written Opinion of the International Searching Authority in International Patent Application No. PCT/JP2016/066586 (dated Aug. 16, 2016).

*Primary Examiner* — Julie Ha
*Assistant Examiner* — Kristina M Hellman
(74) *Attorney, Agent, or Firm* — Leydig, Voit & Mayer, Ltd.

(57) ABSTRACT

The invention provides a method of efficiently and stably producing α-form crystal of reduced glutathione, and a preservation method thereof. According to the invention, development of β-form crystal and/or transition to β-form crystal of reduced glutathione are suppressed by the coexistence of at least one kind of compound selected from the group of aliphatic amino acid, sulfur-containing amino acid, aromatic amino acid, an analogous compound and dipeptide, as a habit modifier, during production and preservation of an aqueous solution or α-form crystal of reduced glutathione.

17 Claims, 1 Drawing Sheet

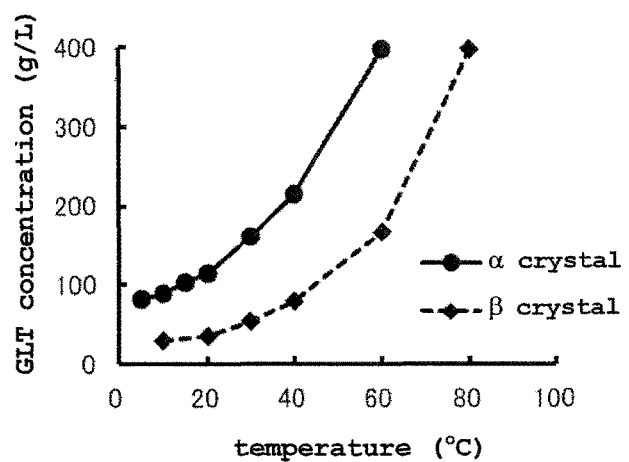

METHOD FOR PRODUCING ALPHA-FORM CRYSTAL OF REDUCED GLUTATHIONE, AND METHOD FOR STORING SAID CRYSTAL

CROSS-REFERENCE TO RELATED APPLICATIONS

This patent application is the U.S. national phase of International Patent Application No. PCT/JP2016/066586, filed Jun. 3, 2016, which claims the benefit of Japanese Patent Application No. 2015-114855, filed on Jun. 5, 2015, which are incorporated by reference in their entireties herein.

TECHNICAL FIELD

The present invention relates to a production method of an α-form crystal of reduced glutathion and a preservation method of the crystal.

BACKGROUND ART

Reduced glutathione is a tripeptide constituted of 3 kinds of amino acids (glutamic acid, cysteine and glycine), and has been utilized as a raw material of a pharmaceutical product or health food, as a material having an anti-oxidative function and a detoxification action. In recent years, the development into a wide variety of markets such as beverages, cosmetics and the like has also been expected.

The crystal of reduced glutathione includes two kinds of crystal polymorphs of α-form crystal and β-form crystal (non-patent document 1). The solubility of the α-form crystal, which is an unstable crystal, and that of the β-form crystal, which is a stable crystal, are markedly different, and the saturated solubility at 10° C. is 89 g/L for the α-form crystal and 30 g/L for the β-form crystal (FIG. 1) (FIGURE). Therefore, the β-form crystal having low solubility is associated with problems that it is difficult to process as a raw material and cannot be handled with ease. Furthermore, a needle-like small β-form crystal is inferior to α-form crystal, which is columnar and easily scaled up, in terms of quality and productivity since it is poor in separability from the mother liquor.

In crystal slurry prepared by adding an α-form crystal to a saturated solution of α-form crystal of reduced glutathione and in a supersaturated solution of reduced glutathione, efficient production of α-form crystal, which is a desirable crystal form, is largely prevented by easy development of β-form crystal, which is a stable crystal. Under such circumstances, the development of a method for suppressing generation of β-type crystal and achieving selective crystallization to give α-type crystal in a supersaturated solution of reduced glutathione has been strongly desired.

On the other hand, as a method of controlling the development of crystal polymorphs of organic compounds including amino acid, addition of a habit modifier may sometimes be effective (patent document 1, non-patent document 2). However, for the habit modifier to function effectively, severe restrictions need to be met; for example, a compound added as a habit modifier needs to have a chemical structure extremely highly similar to that of the object compound (non-patent document 2), and further, a habit modifier needs to have a molecular weight the same as or slightly smaller than that of the object compound (non-patent document 3) and the like. Because of these restrictions, compounds with low structural similarity or compounds with molecular weights far apart from that of the object compound are generally excluded from the search targets of the habit modifier.

Regarding peptides composed of two or more amino acids such as reduced glutathione, an example in which development of crystal polymorphs is controlled by adding a habit modifier has not been known heretofore.

DOCUMENT LIST

Patent Document

Patent document 1: JP-A-2010-59125

Non-Patent Documents

Non-patent document 1: Yamasaki, K. et al., Bunseki Kagaku, 18(7), p 874-878 (1969)
Non-patent document 2: Kuroda, K. et al., Yakugaku Zasshi, 99, p 745-751 (1979)
Non-patent document 3: Momonaga, M. et al., Kagaku Kogaku Ronbunshu, 18(5) p 553-561 (1992)

SUMMARY OF THE INVENTION

Problems to be Solved by the Invention

The problem of the present invention is to provide a method of efficiently and stably producing an α-form crystal of reduced glutathione superior in both quality and productivity, and a preservation method thereof.

Means of Solving the Problems

The present inventors have conducted studies in an attempt to solve the aforementioned problem and found that the development of β-form crystal and transition to β-form crystal are remarkably inhibited by the coexistence of a habit modifier and an aqueous solution of reduced glutathione and α-form crystal, and that the development of β-form crystal and transition to β-form crystal are remarkably suppressed and form crystal can be produced efficiently and stably by crystallizing reduced glutathione as α-form crystals in the coexistence of a habit modifier, when compared to no addition of a habit modifier, which resulted in the completion of the present invention.

Accordingly, the present invention provides the following.

[1] A habit modifier for suppressing development of a β-form crystal of reduced glutathione and/or transition of an α-form crystal to a β-form crystal of reduced glutathione, which habit modifier is composed of at least one compound selected from the group consisting of aliphatic amino acid, sulfur-containing amino acid, aromatic amino acid, an analogous compound and dipeptide.
[2] An α-form crystal of reduced glutathione comprising the habit modifier of the above-mentioned [1].
[3] The crystal of the above-mentioned [2], wherein a content of the habit modifier is 0.01-10 wt % relative to the α-form crystal of reduced glutathione.
[4] A production method of an α-form crystal of reduced glutathione, comprising a step of adding the habit modifier of the above-mentioned [1] to an aqueous solution containing the reduced glutathione, and a step of crystallizing reduced glutathione as an α-form crystal.

[5] The method of the above-mentioned [4], wherein an amount of the habit modifier to be added is 0.01-10 wt % relative to the reduced glutathione.
[6] A preservation method of an aqueous solution of reduced glutathione, comprising a step of adding the habit modifier of the above-mentioned [1] to the aqueous solution of reduced glutathione.
[7] The method of the above-mentioned [6], wherein an amount of the habit modifier to be added is 0.01-10 wt % relative to the reduced glutathione.
[8] A preservation method of an α-form crystal of reduced glutathione, comprising a step of adding the habit modifier of the above-mentioned [1] to the α-form crystal of reduced glutathione.
[9] The method of the above-mentioned [8], wherein an amount of the habit modifier to be added is 0.01-10 wt % relative to the reduced glutathione.

Effect of the Invention

According to the present invention, development of β-form crystal and transition of α-form crystal to β-form crystal are remarkably suppressed by the coexistence of a particular habit modifier during production (crystallization) and preservation of α-form crystal of reduced glutathione, and α-form crystal of reduced glutathione can be produced efficiently and stably.

BRIEF DESCRIPTION OF THE DRAWINGS

FIG. 1 The FIGURE shows solubility curves of α-form crystal of reduced glutathione and β-form crystal, wherein the vertical axis shows solubility (g/L) of each crystal in water at each temperature, and the horizontal axis shows temperature (° C.).

DESCRIPTION OF EMBODIMENTS

The present invention is explained in detail in the following.

Definition

In the present specification, the "reduced glutathione" means tripeptide constituted of glutamic acid, cysteine and glycine, as described above. Reduced glutathione to be used in the present invention may be obtained by any production method. For example, one obtained by the method described in JP-B-57-016196 and the like can be mentioned.

The "habit modifier" generally means an additive to be added to change the crystal habit of the mother compound and prevent transition of polymorphs. In the present invention, it particularly means a compound that suppresses development of β-form crystal of reduced glutathione and inhibits transition of α-form crystal to β-form crystal of reduced glutathione, during production and preservation of α-form crystal of reduced glutathione. Examples of the habit modifier to be used in the present invention include aliphatic amino acids such as alanine, proline and the like, sulfur-containing amino acids such as cysteine and the like, aromatic amino acids such as phenylalanine, tryptophan and the like, analogous compounds such as oxidized glutathione and the like, dipeptides such as alanyl cysteine and the like, and the like. Of these, at least one habit modifier selected from the group consisting of L-cysteine, L-alanine, L-phenylalanine, L-tryptophan, D-proline, oxidized glutathione and L-alanyl-L-cysteine is particularly preferable. While the habit modifier may be obtained by any production method, for example, one obtained by a chemical synthesis method, an extraction method or a fermentation method can be mentioned.

In the present specification, the "aliphatic amino acid" means a hydrophobic amino acid not containing aromatic amino acid. Examples of the aliphatic amino acid include glycine, alanine, valine, leucine, isoleucine, proline and the like. Of these, L-alanine and D-proline are preferable.

In the present specification, the "sulfur-containing amino acid" means an amino acid having a sulfur atom in the structure thereof. Examples of the sulfur-containing amino acid include cysteine, homocysteine, methionine and the like. Of these, L-cysteine is preferable.

In the present specification, the "aromatic amino acid" means a hydrophobic amino acid having an aromatic ring and an aromatic heterocycle. Examples of the aromatic amino acid include phenylalanine, tryptophan, tyrosine and the like. Of these, L-phenylalanine and L-tryptophan are preferable.

In the present specification, the "analogous compound" means a compound similar to reduced glutathione in the molecular biological properties such as receptor binding property and the like, and the structure, but having a composition in which an atom or atomic group constituting reduced glutathione is substituted by another atom or atomic group. Examples of the analogous compound include oxidized glutathione, N-L-cysteinylglycine, γ glutamylcysteine and the like. Of these, oxidized glutathione is preferable.

In the present specification, the "oxidized glutathione" means a molecule in which two molecules of reduced glutathione are linked by a disulfide bond. In the following, oxidized glutathione is sometimes to be abbreviated as "GSSG".

In the present specification, the "dipeptide" means a molecule in which two molecules of amino acid are linked by a peptide bond. Examples of the dipeptide include L-alanine-L-glutamine, L-alanyl-L-cysteine and the like. Of these, L-alanyl-L-cysteine is preferable.

In the present specification, the "aqueous solution" means a solution containing water alone as a solvent, or a solution containing water as a main solvent. The aqueous solution may contain, for example, water-soluble organic solvents such as methanol, ethanol, propanol, acetone and the like, as long as the effect of the present invention is not impaired.

In the present specification, the "aqueous reduced glutathione solution" or "aqueous solution containing reduced glutathione" is an aqueous solution containing at least dissolved reduced glutathione, and may be a solution in which reduced glutathione is completely dissolved, or may contain α-form crystal of reduced glutathione in addition to the dissolved reduced glutathione.
(Preservation Method of the Aqueous Reduced Glutathione Solution of the Present Invention)

To suppress, in an aqueous reduced glutathione solution, development of β-form crystal, which is a stable crystal having low solubility and easily precipitated in an aqueous solution, the present invention provides a preservation method of an aqueous reduced glutathione solution comprising making any one kind or plural kinds of compounds from aliphatic amino acid, sulfur-containing amino acid, aromatic amino acid, an analogous compound and dipeptide coexist as a habit modifier (hereinafter to be referred to as "the preservation method of aqueous solution of the present invention"). As the habit modifier, those mentioned above can be preferably used.

The aqueous reduced glutathione(-containing) solution may contain at least one solute other than the habit modifier, which is selected from the group consisting of aliphatic amino acid, sulfur-containing amino acid, aromatic amino acid, an analogous compound and dipeptide, as long as the effect of the present invention is not impaired. Examples of such solute include salts and buffering agents. Furthermore, the aqueous reduced glutathione(-containing) solution may also be a supernatant of a fermentation liquid containing reduced glutathione, a reaction mixture for producing reduced glutathione or the like. Examples of the aforementioned salt include sodium chloride, sodium sulfate and the like, and examples of the aforementioned buffering agent include sodium acetate, sodium hydrogen carbonate and the like. A method of making coexistence of a habit modifier is not particularly limited, and a habit modifier may be added to an aqueous reduced glutathione solution, or an aqueous reduced glutathione solution may be added to a habit modifier. When a solid habit modifier is added, it is preferably dissolved after addition to an aqueous reduced glutathione solution. In a process of producing reduced glutathione by a fermentation method, an extraction method or a chemical synthesis method, the habit modifier in the present invention may coexist in any step, as long as the production of reduced glutathione is not inhibited. Furthermore, using a raw material containing a habit modifier in the present invention, the reduced glutathione produced from the raw material can also concurrently contain the habit modifier in the present invention.

In the preservation method of an aqueous solution of the present invention, the development of β-form crystal and/or transition of α-form crystal to β-form crystal can be suppressed for a longer time in the coexistence of a habit modifier, compared to non-coexistence thereof.

In the preservation method of an aqueous solution of the present invention, the temperature of the aqueous reduced glutathione solution is not particularly limited as long as the development of β-form crystal and/or transition of α-form crystal to β-form crystal do/does not occur. However, a lower temperature is preferable for suppressing the transition. While the temperature of the aqueous reduced glutathione solution free of development of β-form crystal and/or transition to β-form crystal varies depending on the kind or concentration of the habit modifier, it is generally not more than 60° C., preferably not more than 40° C., more preferably not more than 25° C., particularly preferably not more than 10° C.

The amount of addition of the habit modifier to be coexistent in the aqueous reduced glutathione solution is preferably not less than 0.01 wt %, more preferably not less than 0.1 wt %, particularly preferably not less than 1 wt %, relative to the reduced glutathione. It is desirably not more than 10 wt %.

Addition of a habit modifier enables suppression of the development of β-form crystal and maintenance of the state of a clear aqueous solution even when the concentration of the reduced glutathione in the aqueous reduced glutathione solution is not less than 30 g/L, which is the saturation solubility of β-form crystal at 10° C. When an aqueous reduced glutathione solution contains α-form crystal, the development of β-form crystal and transition to β-form crystal can be prevented even when the concentration of reduced glutathione in the system is not less than 30 g/L.

A preferable amount of the habit modifier to be added can be determined, for example, as follows. A habit modifier is added at not more than about 5 wt % to an aqueous reduced glutathione solution, and the mixture is stirred for a given time. The crystals precipitated during stirring are observed under a microscope, and it is judged whether the crystals are all α-form crystals or development of β-form crystal or transition to β-form crystal has occurred. Since the shape of α-form crystal, which is a large columnar crystal, is markedly different from that of β-form crystal, which is a small needle crystal, they can easily be distinguished by microscopic observation. To quantitatively grasp the state of contamination with β-form crystal, a part is separated and the obtained crystals are dissolved in water at 25° C. to 100 g/L. After maintaining with stirring for a sufficient time, the solution is tested by a visible absorbance measurement method by using a cell having a layer length of 1 cm with water as a control, and the permeability is measured at 430 nm and turbidity is confirmed. The permeability can be expressed by permeability (T %) 430 nm=$100\times10^{-A}$ (A=Abs: 430 nm, 1 cm). When β-form crystal having low solubility is present, the permeability of the solution is lowered since the crystals left undissolved are detected as turbidity. Since the development of β-form crystal causes crystallization and a lower concentration of reduced glutathione in the solution in the slurry than that of a solution containing α-form crystal alone, the kind of the coexisting crystals can also be distinguished by measuring the concentration of reduced glutathione in the mother liquor from which the coexisting crystals have been removed. The concentration of reduced glutathione in the mother liquor is measured by removing the coexisting crystals by filtration and the like, diluting same with mobile phase to a given concentration, maintaining with stirring for a sufficient time, and measuring the concentration under the following HPLC conditions.

HPLC conditions
column: Inertsil ODS-3 inner diameter 3.0 mm, length 150 mm
column temperature: 35° C.
detector: UV detector wavelength 210 nm
mobile phase composition: sodium 1-heptanesulfate/potassium dihydrogen phosphate/phosphoric acid/methanol The kind and content of each habit modifier component contained in the aqueous reduced glutathione solution can also be measured, for example, by precisely weighing a sample by about 0.25 g, dissolving same in pure water, fixing same to a constant volume of 25 mL, collecting 1 mL, to which dilution buffer is added, and the mixture is fixed to a constant volume of 10 mL, the constant volume solution is centrifuged at 10000 rpm for 5 min, and the supernatant is introduced into Amino Acid Analyzer JLC-500V (manufactured by JEOL Ltd.) and measured according to the description of instruction manual.

(α-Form Crystal of Reduced Glutathione of the Present Invention)

The present invention provides α-form crystal of reduced glutathione, which contains the aforementioned habit modifier (hereinafter to be also referred to as "the α-form crystal of the present invention").

The α-form crystal of reduced glutathione is a crystal having peaks at diffraction angles 2θ of 6.3°, 12.6°, 13.8°, 16.2°, 22.3°, 25.7°, 30.1°, 31.9°, 32.0° and 33.5°, by powder X-ray diffraction.

The content of a habit modifier to be contained in the α-form crystal of reduced glutathione is preferably not less than 0.01 wt %, more preferably not less than 0.1 wt %, particularly preferably not less than 1.0 wt %, relative to the α-form crystal of reduced glutathione. It is desirably not more than 10 wt %.

Since the aforementioned habit modifier is contained, transition of the α-form crystal of the present invention to β-form crystal having low solubility and difficult to process as a raw material is suppressed.

The amount of the habit modifier to be contained in the α-form crystal of reduced glutathione of the present invention can be determined by diluting the α-form crystal of the present invention with mobile phase to a given concentration, maintaining with stirring for a sufficient time, and measuring the concentration under the following HPLC conditions.

HPLC Conditions
column: YMC Triart C18 inner diameter 3.0 mm, length 150 mm
column temperature: 40° C.
detector: fluorescence detector excitation wavelength 360 nm/fluorescence wavelength 440 nm
mobile phase composition: trisodium citrate dihydrate/anhydrous sodium sulfate/n-propanol/sodium lauryl sulfate The kind and content of each habit modifier component contained in the α-form crystal of the present invention can also be measured, for example, by precisely weighing a sample by about 0.25 g, dissolving same in pure water, fixing same to a constant volume of 25 mL, collecting 1 mL, to which dilution buffer is added, and the mixture is fixed to a constant volume of 10 mL, the constant volume solution is centrifuged at 10000 rpm for 5 min, and the supernatant is introduced into Amino Acid Analyzer JLC-500V (manufactured by JEOL Ltd.) and measured according to the description of instruction manual.

(Preservation Method of α-Form Crystal of Reduced Glutathione of the Present Invention)

To suppress, in α-form crystal of reduced glutathione, transition to β-form crystal having low solubility and difficult to process as a raw material, the present invention provides a preservation method of α-form crystal of reduced glutathione comprising making one kind or plural kinds selected from the group consisting of aliphatic amino acid, sulfur-containing amino acid, aromatic amino acid, an analogous compound and dipeptide coexist as a habit modifier (hereinafter to be referred to as "the preservation method of α-form crystal of the present invention"). As a habit modifier, those mentioned above can be preferably used.

The α-form crystal of reduced glutathione may contain reduced glutathione, and one kind or plural kinds of substances other than a habit modifier, which are selected from the group consisting of aliphatic amino acid, sulfur-containing amino acid, aromatic amino acid, an analogous compound and dipeptide, as long as the effect of the present invention is not impaired. Examples of such substance include salt, organic solvent and analogous compound.

To suppress transition of α-form crystal to β-form crystal of reduced glutathione in the preservation method of the α-form crystal of the present invention, a habit modifier is made to coexist with the α-form crystal of reduced glutathione. A method of making a habit modifier to coexist with α-form crystal of reduced glutathione is not limited, and α-form crystal of reduced glutathione may be suspended in a solution of a habit modifier, and the crystal is separated to give a crystal in which the habit modifier coexists, or a solution containing a habit modifier may be sprayed on α-form crystal of reduced glutathione to give a crystal in which the habit modifier coexists.

In the preservation method of the α-form crystal of the present invention, the development of β-form crystal and/or transition of α-form crystal to β-form crystal can be suppressed for a longer time in the coexistence of a habit modifier, compared to non-coexistence thereof.

In the preservation method of the α-form crystal of the present invention, the preservation temperature of the α-form crystal is not particularly limited as long as the development of β-form crystal and/or transition of α-form crystal to β-form crystal do/does not occur. However, a lower temperature is preferable for suppressing transition. While the preservation temperature of the α-form crystal of reduced glutathione free of development of β-form crystal and/or transition to β-form crystal varies depending on the kind or concentration of the habit modifier, specifically, it is generally not more than 60° C., preferably not more than 40° C., more preferably not more than 25° C., particularly preferably not more than 10° C.

The addition amount of the habit modifier to be coexistent in the α-form crystal of reduced glutathione is preferably not less than 0.01 wt %, more preferably not less than 0.1 wt %, particularly preferably not less than 1.0 wt %, relative to the α-form crystal of reduced glutathione. It is desirably not more than 10 wt %.

The amount of the habit modifier to be coexisting with α-form crystal of reduced glutathione can be determined by diluting α-form crystal of reduced glutathione in coexistence with a habit modifier with mobile phase to a given concentration, maintaining with stirring for a sufficient time, and measuring the concentration under the following HPLC conditions.

HPLC Conditions
column: YMC Triart C18 inner diameter 3.0 mm, length 150 mm
column temperature: 40° C.
detector: fluorescence detector excitation wavelength 360 nm/fluorescence wavelength 440 nm
mobile phase composition: trisodium citrate dihydrate/anhydrous sodium sulfate/n-propanol/sodium lauryl sulfate The kind and content of each habit modifier component contained in the α-form crystal of reduced glutathione can also be measured, for example, by precisely weighing a sample by about 0.25 g, dissolving same in pure water, fixing same to a constant volume of 25 mL, collecting 1 mL, to which dilution buffer is added, and the mixture is fixed to a constant volume of 10 mL, the constant volume solution is centrifuged at 10000 rpm for 5 min, and the supernatant is introduced into Amino Acid Analyzer JLC-500V (manufactured by JEOL Ltd.) and measured according to the description of instruction manual.

(Production Method of α-Form Crystal of Reduced Glutathione of the Present Invention)

The present invention provides a production method of α-form crystal of reduced glutathione, comprising crystallizing reduced glutathione as α-form crystals from an aqueous reduced glutathione solution in the coexistence of at least one habit modifier selected from the group consisting of aliphatic amino acid, sulfur-containing amino acid, aromatic amino acid, an analogous compound and dipeptide to give α-form crystal of reduced glutathione (hereinafter to be referred to as "the production method of the present invention"). As a habit modifier, those mentioned above can be preferably used.

To achieve coexistence of a habit modifier with reduced glutathione, a habit modifier may be added to an aqueous reduced glutathione solution, or reduced glutathione may be added to a habit modifier solution. The habit modifier to be added may be a solid or a solution. When a solid habit modifier is added, it is preferably dissolved after addition to an aqueous reduced glutathione solution. In a process of producing reduced glutathione by a fermentation method, an extraction method or a chemical synthesis method, the habit modifier in the present invention may coexist in any step as long as the production of reduced glutathione is not inhibited. Furthermore, using a raw material containing a habit modifier in the present invention, the reduced glutathione produced from the raw material can also concurrently contain the habit modifier in the present invention.

In the production method of the present invention, a habit modifier may be added to an aqueous reduced glutathione solution prior to crystallization, or may be added after precipitation of α-form crystal of reduced glutathione and before transition to β-form crystal begins.

While the crystallization method is not particularly limited, concentration crystallization in which crystallization is performed by concentrating an aqueous reduced glutathione solution, cooling crystallization in which crystallization is performed by cooling an aqueous reduced glutathione solution, or poor solvent crystallization in which crystallization is performed by adding a poor solvent to an aqueous reduced glutathione solution, or a combination of these methods. Examples of the poor solvent include alcohol having 1-6 carbon atoms, as well as acetone, methyl ethyl ketone and diethyl ketone.

Crystals of reduced glutathione are precipitated by concentrating or cooling an aqueous reduced glutathione solution to increase the concentration of reduced glutathione to not less than the saturated solubility, or lowering the saturated solubility by adding a poor solvent to an aqueous reduced glutathione solution. In this case, the coexistence of at least one habit modifier selected from the group consisting of aliphatic amino acid, sulfur-containing amino acid, aromatic amino acid, an analogous compound and dipeptide suppresses the development of β-form crystal and transition of α-form crystal to β-form crystal for a longer time, compared to non-coexistence thereof. Therefore; α-form crystals can be obtained efficiently and stably.

In another embodiment, α-form crystal of reduced glutathione may be added as a seed crystal prior to the concentration, cooling operation or poor solvent addition of an aqueous reduced glutathione solution, or during these operations. An α-form crystal of reduced glutathione can be obtained, for example, by crystallization from an aqueous reduced glutathione solution at not more than 25° C.

When a crystal of reduced glutathione is precipitated from an aqueous reduced glutathione solution, development of β-form crystal of reduced glutathione, or transition of α-form crystal to β-form crystal easily occurs in the absence of a habit modifier. This phenomenon is more remarkable when the temperature is high. In contrast, the temperature at which transition of reduced glutathione to β-form crystal can be raised in the coexistence of a habit modifier, compared to the non-coexistence thereof. Even when the temperature is the same, the time before occurrence of transition of α-form crystal to β-form crystal of reduced glutathione can be extended.

In one embodiment of the production method of the present invention, a part of reduced glutathione is precipitated as α-form crystals by concentrating an aqueous reduced glutathione solution and the resulting slurry is cooled to further precipitate the dissolved reduced glutathione as α-form crystals. In this case, a habit modifier is desirably added before or after concentration of the aqueous reduced glutathione solution, or at least before crystallization of reduced glutathione.

In the production method of the present invention, the temperature at which reduced glutathione is crystallized as α-form crystals is not particularly limited as long as the development of β-form crystal and/or transition of α-form crystal to β-form crystal do/does not occur. However, a lower temperature is preferable in teams of the yield. Since the temperature at which reduced glutathione is crystallized as α-form crystals, and development of β-form crystal and/or transition of α-form crystal to β-form crystal do/does not occur varies depending on the kind or concentration of the habit modifier, it is desirably determined as appropriate. It is preferably not more than 40° C., more preferably not more than 25° C., particularly preferably not more than 10° C.

The concentration of the habit modifier to be coexistent in the aqueous reduced glutathione solution, for example, when the crystallization temperature is 25° C. and the crystallization time is not less than 24 hr is preferably not less than 0.01 wt %, more preferably not less than 0.1 wt %, particularly preferably not less than 1.0 wt %, relative to the reduced glutathione. It is desirably not more than 10 wt %. However, the inhibitory effect of the habit modifier on the development of β-form crystal and transition to β-form crystal can vary depending on the kind of the habit modifier, temperature at which crystallization is performed, the kind and concentration of the reduced glutathione and components other than the habit modifier to be contained in the aqueous reduced glutathione solution, and the like. Therefore, a preferable amount of the habit modifier to be added is desirably determined as appropriate according to the aqueous reduced glutathione solution to which the present invention is applied, the kind and concentration of the habit modifier to be used, and crystallization temperature. To extend the time before occurrence of the development of β-form crystal, or transition of α-form crystal to β-form crystal, it is preferable to increase the concentration of the habit modifier.

After precipitation of α-form crystal of reduced glutathione as mentioned above, the crystals are separated from the mother liquor, whereby α-form crystal of reduced glutathione is obtained. Excessive habit modifier and impurities can be removed from the α-form crystal by recrystallization, crystal washing and the like. The obtained α-form crystals are desirably dried to prevent further transition to β-form crystals.

While the drying method is not limited, for example, drying under reduced pressure and ventilation drying can be used. The drying temperature may be a temperature at which reduced glutathione is not decomposed, and is preferably not more than 100° C., more preferably not more than 60° C., particularly preferably not more than 25° C. The α-form crystal of reduced glutathione after drying can be appropriately packaged into a final product.

EXAMPLES

While the present invention is explained more specifically by way of Examples, the present invention is not limited by the descriptions thereof.

Example 1

Confirmation Test of Suppressive Effect on Transition to β-Form Crystal by the Addition of Habit Modifier During Preservation of α-Form Crystal of Reduced Glutathione α-Form crystals of reduced glutathione (9 g) and water (30 mL) were mixed in a glass bottle. To the prepared solution were added 0.45 g each of L-alanine (hereinafter sometimes to be abbreviated as L-Ala), L-cysteine (hereinafter sometimes to be abbreviated as L-Cys), L-phenylalanine (hereinafter sometimes to be abbreviated as L-Phe), L-tryptophan (hereinafter sometimes to be abbreviated as L-Trp), D-proline (hereinafter sometimes to be abbreviated as D-Pro), L-alanyl-L-cysteine (hereinafter sometimes to be abbreviated as AlaCys) or oxidized glutathione (GSSG), and dissolved therein. The glass bottle was shaken in a tray dryer set to 25° C. for 24 hr. After 24 hr, crystals in the slurry were microscopically observed and the presence or absence of transition to β-form crystal was determined.

As a result, suppression of the transition of α-form crystal to β-form crystal was found in the coexistence of any compound of L-alanine, L-cysteine, L-phenylalanine, L-tryptophan, D-proline, L-alanyl-L-cysteine and oxidized glutathione.

Example 2

Confirmation Test of Suppressive Effect on Development of β-Form Crystal by the Addition of Habit Modifier During Preservation of α-Form Crystal of Reduced Glutathione In an aqueous solution (10 mL) containing 5 wt % (relative to reduced glutathione) each of L-alanine, L-cysteine, L-phenylalanine, L-tryptophan, L-alanyl-L-cysteine or oxidized glutathione (GSSG), or L-histidine hydrochloride (hereinafter sometimes to be abbreviated as L-His) for a comparison test was immersed α-form crystal (5 g) of reduced glutathione, and then, the total amount of crystals obtained by separation therefrom using a membrane filter was packed in a bottle and the bottle was left standing in a thermostatic tank such that the temperature of the crystal portion was 40° C. After 3 hr, the crystals (each 1 g) were dissolved in water (10 mL) at 25° C., the permeability at 430 nm was measured, and the turbidity was confirmed to determine the presence or absence of transition to β-form crystal. The results are shown in Table 1. In the habit modifier effect in Table 1, ○ shows suppression of development of β-form crystal, and x shows development of β-form crystal.

TABLE 1

| | substance added | | | | | | | |
|---|---|---|---|---|---|---|---|---|
| | L-Ala | L-Cys | L-Phe | L-Trp | AlaCys | GSSG | L-His | none |
| permeability (%) | 100 | 100 | 100 | 99 | 99 | 99 | 95 | 87 |
| habit modifier effect | ○ | ○ | ○ | ○ | ○ | ○ | x | x |

As shown in Table 1, the development of β-form crystal was suppressed by the coexistence of α-form crystal of reduced glutathione and L-alanine, L-cysteine, L-phenylalanine, L-tryptophan, L-alanyl-L-cysteine or oxidized glutathione (GSSG).

Example 3

Confirmation Test of Effect of the Addition of Habit Modifier During Preservation of Aqueous Reduced Glutathione Solution Reduced glutathione (100 g) was measured in a 1 L beaker, water was added to make 1 L. The mixture was heated at 40° C. to completely dissolve the crystals, and filtered through a membrane filter. To the prepared aqueous reduced glutathione solution (100 g/L) were added 5 wt % (relative to reduced glutathione) each of a compound confirmed in [Example 1] to have a habit modifier effect, or L-histidine hydrochloride for a comparison test, and each of the mixture was cooled to 10° C. and stirred for 24 hr. After 24 hr, the supernatant thereof was filtered through a filter with a pore size of 0.45 μm, the concentration of reduced glutathione in the supernatant was measured by HPLC, and the presence or absence of the development of β-form crystal was determined based on the changes in the concentration. The results are shown in Table 2. In the habit modifier effect in Table 2, ○ shows suppression of the development of β-form crystal, and x shows development of β-form crystal.

TABLE 2

| | substance added | | | | | | | |
|---|---|---|---|---|---|---|---|---|
| | L-Ala | L-Cys | L-Phe | L-Trp | D-Pro | AlaCys | GSSG | L-His | none |
| concentration [g/L] | 111.1 | 111.0 | 111.1 | 111.6 | 111.7 | 108.2 | 110.8 | 41.7 | 28.9 |
| habit modifier effect | ○ | ○ | ○ | ○ | ○ | ○ | ○ | x | x |

Respective aqueous solutions of reduced glutathione containing L-alanine, L-cysteine, L-phenylalanine, L-tryptophan, D-proline, L-alanyl-L-cysteine or oxidized glutathione (GSSG) suppressed development of β-form crystal.

Example 4

Consideration of amount to be added of habit modifier necessary for suppressing development of β-form crystal during preservation of aqueous reduced glutathione solution Reduced glutathione (100 g) was measured in a 1 L beaker, water was added to make 1 L. The mixture was heated at 40° C. to completely dissolve the crystals, and filtered through a membrane filter. To the prepared aqueous reduced glutathione solution (100 g/L) was added 0.01 wt %-1 wt % (relative to reduced glutathione) of L-alanine, which was confirmed to have a habit modifier effect, and the mixture was cooled to 10° C. and stirred for 15 hr. After 15 hr, the supernatant was filtered through a filter with a pore size of 0.45 μm, the concentration of reduced glutathione in the supernatant was measured by HPLC, and the presence or absence and the degree of the development of β-form crystal were determined by observing the changes in the concentration of reduced glutathione. The results of the elapsed time and changes in the concentration of reduced glutathione due to the presence or absence of a habit modifier are shown in Table 3.

TABLE 3

| habit modifier (amount added) | elapsed time (h) | |
|---|---|---|
| | 0 | 15 |
| no habit modifier | 94.2* | 73.9* |
| L-alanine (0.01%) | 94.2* | 89.2* |
| L-alanine (0.1%) | 94.2* | 91.2* |
| L-alanine (1.0%) | 94.2* | 92.6* |

*concentration (g/L) of reduced glutathione

It was found that an aqueous solution of reduced glutathione without addition of L-alanine contained about 20% of reduced glutathione as β-form crystal 15 hr later. On the other hand, it was found that an aqueous solution added with L-alanine as a habit modifier showed suppressed development of β-form crystal. In addition, it was found that a larger amount of L-alanine made the development of β-form crystal less likely to occur.

It was found that the amount of addition of L-alanine as a habit modifier to coexist in an aqueous solution of reduced glutathione is preferably not less than 0.01 wt %, more preferably not less than 0.1 wt %, particularly preferably not less than 1 wt %, relative to the reduced glutathione.

Example 5

Production Method (1) of α-Form Crystal of Reduced Glutathione

Reduced glutathione (50 g) and water (500 mL) were added to a 1 L beaker. To the prepared solution were added 2.5 g each of L-alanine, L-cysteine or oxidized glutathione, and the mixture was heated at 40° C. to completely dissolve the crystals and filtered through a membrane filter. The prepared solution (filtrate) was concentrated by an evaporator such that the concentration of reduced glutathione was not less than the saturation solubility of α-form crystal to perform concentration crystallization of reduced glutathione. The concentrate was cooled to 25° C. and stirred for 24 hr, the crystals in the slurry were microscopically observed, and the presence or absence of transition to β-form crystal was determined.

As a result, crystallization added with L-alanine, L-cysteine or oxidized glutathione produced α-form crystal alone, without developing β-form crystal.

Example 6

Production Method (2) of α-Form Crystal of Reduced Glutathione

Reduced glutathione (50 g) and water (500 mL) were added to a 1 L beaker. To the prepared solution were added 10 wt % each of L-alanine or L-cysteine relative to the reduced glutathione, and the mixture was heated at 40° C. to completely dissolve the crystals and filtered through a membrane filter. The prepared solution (filtrate) was concentrated by an evaporator such that the concentration of reduced glutathione was not less than the saturation solubility of α-form crystal to perform concentration crystallization of reduced glutathione. The concentrate was cooled to 25° C. and stirred for 24 hr, the crystals in the slurry were microscopically observed, and the presence or absence of transition to β-form crystal was determined.

As a result, crystallization added with L-alanine or L-cysteine produced α-form crystal alone, without developing β-form crystal.

It was found that the crystals obtained by crystallization added with 10 wt % each of L-alanine or L-cysteine were both α-form crystals of reduced glutathione having peaks at diffraction angles 2θ of 6.3°, 12.6°, 13.8°, 16.2°, 22.3°, 25.7°, 30.1°, 31.9°, 32.0° and 33.5°, by powder X-ray diffraction.

INDUSTRIAL APPLICABILITY

According to the present invention, development of β-form crystal and transition of α-form crystal to β-form crystal are remarkably suppressed by the coexistence of a particular habit modifier or a preservative during production (crystallization) and preservation of α-form crystal of reduced glutathione, and α-form crystal of reduced glutathione can be produced efficiently and stably. According to the present invention, moreover, since α-form crystal of reduced glutathione superior in both quality and productivity can be supplied stably, it is useful in a wide variety of fields such as pharmaceutical products, foods, cosmetics and the like.

This application is based on a patent application No. 2015-114855 filed in Japan, the contents of which are incorporated in full herein.

The invention claimed is:

1. A production method of an α-form crystal of reduced glutathione, comprising a step of adding a habit modifier to an aqueous solution containing the reduced glutathione, and a step of crystallizing reduced glutathione as an α-form crystal, wherein the habit modifier is at least one compound selected from the group consisting of an aliphatic amino acid, a sulfur-containing amino acid, an aromatic amino acid, a dipeptide, oxidized glutathione, N-L-cysteinylqlycine, and γ glutamylcysteine.

2. The method according to claim 1, wherein the habit modifier is added in an amount of 0.01-10 wt % relative to the reduced glutathione.

3. The method according to claim 1, wherein the habit modifier is an aliphatic amino acid.

4. The method according to claim 3, wherein the aliphatic amino acid is selected from the group consisting of glycine, alanine, valine, leucine, isoleucine, and proline.

5. The method according to claim 3, wherein the aliphatic amino acid is L-alanine or D-proline.

6. The method according to claim 1, wherein the habit modifier is a sulfur-containing amino acid.

7. The method according to claim 6, wherein the sulfur-containing amino acid is selected from the group consisting of cysteine, homocysteine, and methionine.

8. The method according to claim 6, wherein the sulfur-containing amino acid is L-cysteine.

9. The method according to claim 1, wherein the habit modifier is an aromatic amino acid.

10. The method according to claim 9, wherein the aromatic amino acid is selected from the group consisting of phenylalanine, tryptophan, and tyrosine.

11. The method according to claim 9, wherein the aromatic amino acid is L-phenylalanine or L-tryptophan.

12. The method according to claim 1, wherein the habit modifier is a dipeptide.

13. The method according to claim 12, wherein the dipeptide is L-alanine-L-glutamine.

14. The method according to claim 12, wherein the dipeptide is L-alanyl-L-cysteine.

15. The method according to claim 1, wherein the habit modifier is oxidized glutathione.

16. The method according to claim 1, wherein the habit modifier is N-L-cysteinylglycine.

17. The method according to claim 1, wherein the habit modifier is γ glutamylcysteine.

* * * * *